(12) United States Patent
Jensen

(10) Patent No.: US 8,548,556 B2
(45) Date of Patent: Oct. 1, 2013

(54) BIOELECTRICAL IMPEDANCE MEASURING APPARATUS

(75) Inventor: Björn Jensen, Hamburg (DE)

(73) Assignee: seca ag (CH)

( * ) Notice: Subject to any disclaimer, the term of this patent is extended or adjusted under 35 U.S.C. 154(b) by 261 days.

(21) Appl. No.: 12/896,547

(22) Filed: Oct. 1, 2010

(65) Prior Publication Data

US 2011/0237926 A1    Sep. 29, 2011

(30) Foreign Application Priority Data

Oct. 1, 2009   (EP) ..................................... 09171978

(51) Int. Cl.
*A61B 5/053*    (2006.01)

(52) U.S. Cl.
USPC ............................. 600/384; 600/393; 600/547

(58) Field of Classification Search
USPC ........ 600/372, 382, 384, 393, 547; D24/133, D24/187
See application file for complete search history.

(56) References Cited

U.S. PATENT DOCUMENTS

| | | | |
|---|---|---|---|
| 3,900,020 A * | 8/1975 | Lock .............................. | 600/548 |
| D254,504 S * | 3/1980 | Myers .......................... | D24/133 |
| 4,557,271 A | 12/1985 | Stoller et al. | |
| 5,817,031 A * | 10/1998 | Masuo et al. ................. | 600/547 |
| 6,280,396 B1 | 8/2001 | Clark | |
| 6,400,983 B1 * | 6/2002 | Cha .............................. | 600/547 |
| 7,262,703 B2 * | 8/2007 | Collins ....................... | 340/573.1 |
| 2004/0059242 A1 | 3/2004 | Masuo et al. | |
| 2004/0158166 A1 * | 8/2004 | Levengood ................... | 600/547 |
| 2007/0208241 A1 * | 9/2007 | Drucker ........................ | 600/323 |
| 2009/0247897 A1 * | 10/2009 | Ashida et al. ................. | 600/547 |

FOREIGN PATENT DOCUMENTS

| | | |
|---|---|---|
| DE | 19532760 A1 | 3/1997 |
| EP | 0998874 A2 | 5/2000 |
| WO | 9701303 | 1/1997 |

* cited by examiner

*Primary Examiner* — Linda Dvorak
*Assistant Examiner* — Erin M Cardinal
(74) *Attorney, Agent, or Firm* — Hovey Williams LLP

(57) ABSTRACT

The present invention provides a bioelectrical impedance measuring apparatus for determining composition data of a human body, the apparatus including a plurality of electrodes and measuring circuitry which inject, through two electrodes, alternating current into the body, and which determine, with two other electrodes on different limbs, the resulting voltages, and which determine therefrom the impedance of body segments. In one apparatus, two hand contact bodies are disclosed, each of which includes a hand seating surface for placement of a hand inner surface thereon, each hand seating surface includes an electrically insulating separating wall extending over a part of the length of the hand seating surface, the separating wall being adapted to project into the space between middle and ring finger when a hand is placed on the hand seating surface, and on both sides of the separating wall an electrode is included.

6 Claims, 4 Drawing Sheets

BIOELECTRICAL IMPEDANCE MEASURING APPARATUS

CROSS-REFERENCE TO RELATED APPLICATION

Figure 1:
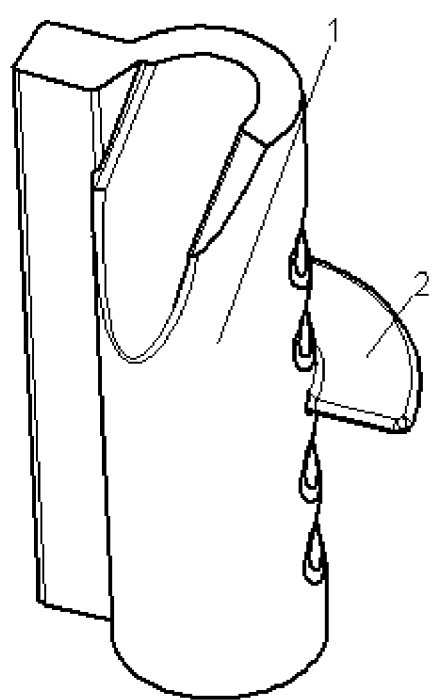

The present application claims the benefit of and priority from European Patent Application Serial No. EP 09171978.1, filed Oct. 1, 2009, the entire disclosure of which is hereby incorporated by reference herein.

BACKGROUND OF THE INVENTION

1. Field of the Invention

The present invention relates to a bioelectrical impedance measuring apparatus for determining composition data of a human body.

2. Discussion of the Prior Art

The conductivity of a human body is strongly influenced by its water content. Since areas of the body which are free of fat, such as muscles and bodily fluids, contain the major part of the water content of the body, while on the other hand fat tissue has a relatively low water content, the determination of the conductivity of a body or of a body segment (or the determination of the reciprocal resistance or impedance of the body or of the body segment) allows to draw conclusions on the relative fat content, at least if further data such as body height and weight of the person are taken into account.

A method and an apparatus for bioelectrical impedance analysis are described for example in WO 97/01303. The apparatus described therein comprises eight electrodes, namely four electrodes for the feet, in each case two electrodes for contacting one foot, and four hand electrodes, in each case two electrodes for contacting one hand of the person. An alternating current is applied through two electrodes which are positioned on different limbs, and the voltage between two other electrodes is measured, which measuring electrodes are likewise positioned on different limbs. By switching over to two other current applying electrodes and voltage measuring electrodes different body segments can be examined consecutively. Furthermore, when current is injected in one hand and in one foot, and voltage is measured between the other electrode on the same hand and the other electrode on the same foot, one side of the body as a whole can be measured.

DE 195 32 760 A1 describes a bioelectrical impedance measuring apparatus having for each limb two electrodes which are attached to the skin with adhesive means, wherein on each limb one electrode is disposed more distant from the torso than the other electrode on the same limb. Current is applied through the electrodes disposed in further distance, and voltage is measured using the closer electrodes. The voltage measurement thus takes place in the current path which may lead to measuring errors since the results depend on variations in the precise positioning of the electrodes.

The bioelectrical impedance measuring apparatus described in WO 97/01303 has a standing platform for both feet on which two electrodes for a contacting the sole of foot for each foot are provided; furthermore, two hand contact bodies are provided for establishing contact with the inner surface of each hand of the user. Each hand contact body has an essentially cylindrical shape so that it may be grasped by a hand, the surface of the palm and the inner surface of the fingers so coming into contact with the surface of the hand contact body. On each hand contact body two electrodes are provided, namely one in the area of the cylinder barrel and the other on the front end face of the cylinder such that when the user grasps the hand contact body the one electrode comes into contact with the palm or the inner surface of the fingers and the other electrode comes into contact with the thumb placed on the front end face. In this manner, by establishing contact at the palm and at the thumb, to a certain degree a decoupling of the current path and of the voltage measuring path is achieved which, however, does not result in a reliable measurement of the impedance. In fact the thumb is particularly moveable so that the point where the current path and the voltage measuring path meet within the body strongly varies with the variable thumb position. Therefore, there is a strong dependence of the measured impedance value on the thumb position.

SUMMARY

It is an object of the present invention to improve a bioelectrical impedance measuring apparatus is such a way that it may be handled more easily by the user while at the same time provides more reliable and more precise measuring values of the impedance.

To achieve this object a bioelectrical impedance measuring apparatus including a plurality of electrodes, measuring circuitry including alternating current sources, voltage measuring circuits, and a control and analysis unit, and hand contact bodies, each of which is shaped in such a manner and provided with electrodes in such a manner that a user, when contacting the hand contact bodies with hands, comes into contact with electrodes for each hand on each respective hand contact body is provided. Each hand contact body includes a hand seating surface for placement of a hand inner surface thereon, and each hand seating surface includes an electrically insulating separating wall extending over a part of the length of the hand seating surface. The separating wall is configured to project into a space between middle and ring finger when a hand is placed on the hand seating surface, with selected ones of the electrodes being disposed on each side of the separating wall such that, when a hand is placed on the hand seating surface, one electrode comes into contact with the small finger and/or ring finger and the other electrode comes into contact with middle finger and/or index finger. Preferred embodiments of the invention are also provided.

According to the invention each hand contact body has a hand seating or supporting surface to place at least part of the palm and the finger inner surfaces thereon. Each hand seating or supporting surface is provided with a separating or dividing wall which is electrically insulating and extends over a part of the length of the seating surface, the separating wall being adapted, when the hand is placed on the hand seating surface, to project into the space between middle finger and ring finger to thereby separate middle finger and ring finger from each other. On both sides of the separating wall and separated by the separating wall a respective electrode is disposed so that one electrode, when the hand is placed on the hand seating surface, has contact with the little finger and/or ring finger of the hand, and the other electrode has contact with the middle finger and/or index finger of the hand.

By this means a well reproducible and reliable positioning of the hand inner surface on the hand contact body is achieved since the separating wall on the hand contact body determines the position of the hand thereon. The separating wall determines the position with respect to the transverse direction of the fingers by projecting into the space between middle and ring finger. Furthermore, the separating wall determines the position with respect to the longitudinal direction of the fingers since the end of the separating wall, which extends only over a part of the length of the hand seating surface, abuts against the hand area between the base of the middle finger and the base of the ring finger. Because the separating wall is electrically insulating any electrical interaction or any possibility of short circuits between the two electrodes are excluded.

In addition it turned out that, by establishing contact of the electrodes on the inner surfaces of the fingers at essentially the same distance from the torso of the user, the current injection through one of the electrodes and the voltage measurement by the other electrode take place at anatomically comparable body portions so that a better reproducible and reliable measurement of the impedance without mutual interference or influence of current path and voltage measuring path may be realized.

In principle more separating walls may be present which are then intended to project into the space between further finger pairs.

In a preferred embodiment the hand seating surface is formed essentially as a plane such that flat hand may be placed thereon, wherein over a part of the plane the separating wall is projecting upright or perpendicularly to the plane in order to, when the hand is placed on the hand seating surface, separate middle finger from ring finger, wherein on each side of the separating wall an electrode is disposed.

In an alternative embodiment the hand seating surface is at least partially curved so that it may be grasped by a hand as a handgrip.

In a preferred embodiment each electrode is provided with an elongated projection extending parallel to the separating wall, which projection is adapted, when a hand is placed on the hand seating surface, to abut on a side surface of a finger. This has the effect that electrical contact is also established on a finger side surface. This ensures that the electrode also has contact with the relative thin skin on a finger side surface which ensures a better reproducible electrical contact as compared to a contact on the inner finger surface only, which inner surface in general has thicker skin portions and in many cases callus.

In a particularly preferred embodiment each electrode is provided with two elongated depressions or troughs extending parallel to the separating wall, which depressions or troughs are adapted to establish contact with the finger side surfaces of two fingers placed in the finger depressions or troughs. By this means a particularly good and reproducible electrical contacting of the finger side surfaces of small finger, ring finger, middle finger and index finger is ensured. The finger depressions or troughs are essentially of complementary shape to average small fingers, ring fingers, middle fingers and index fingers so that each trough or depression may receive one of the fingers.

This summary is provided to introduce a selection of concepts in a simplified form that are further described below in the detailed description of the preferred embodiments. This summary is not intended to identify key features or essential features of the claimed subject matter, nor is it intended to be used to limit the scope of the claimed subject matter.

Various other aspects and advantages of the present invention will be apparent from the following detailed description of the preferred embodiments and the accompanying drawing figures.

BRIEF DESCRIPTION OF THE DRAWING FIGURES

Figure 2:
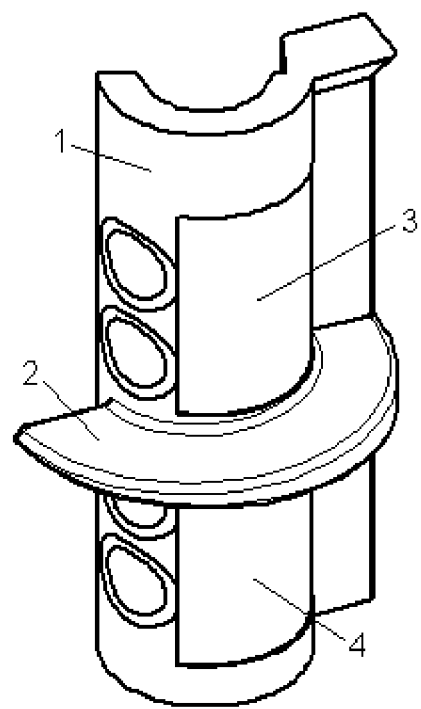
Figure 3:
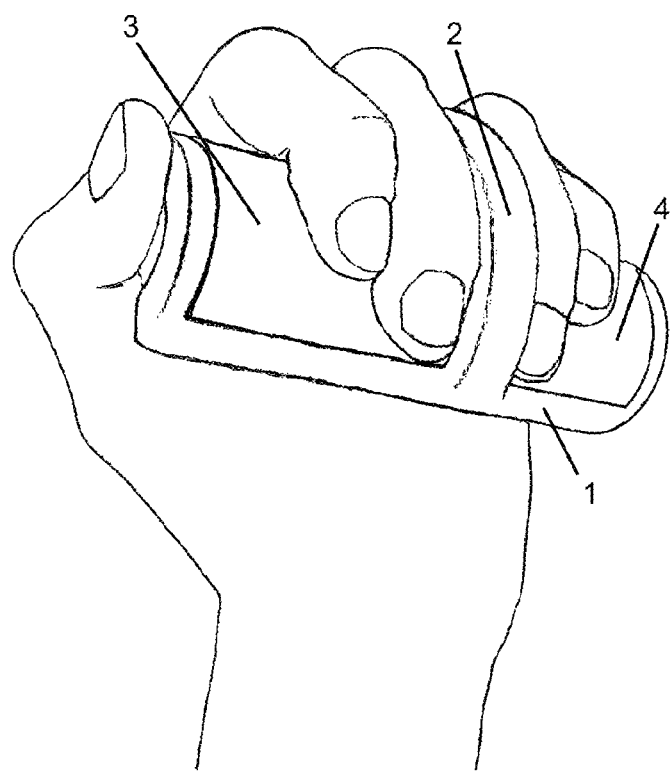
Figure 4:
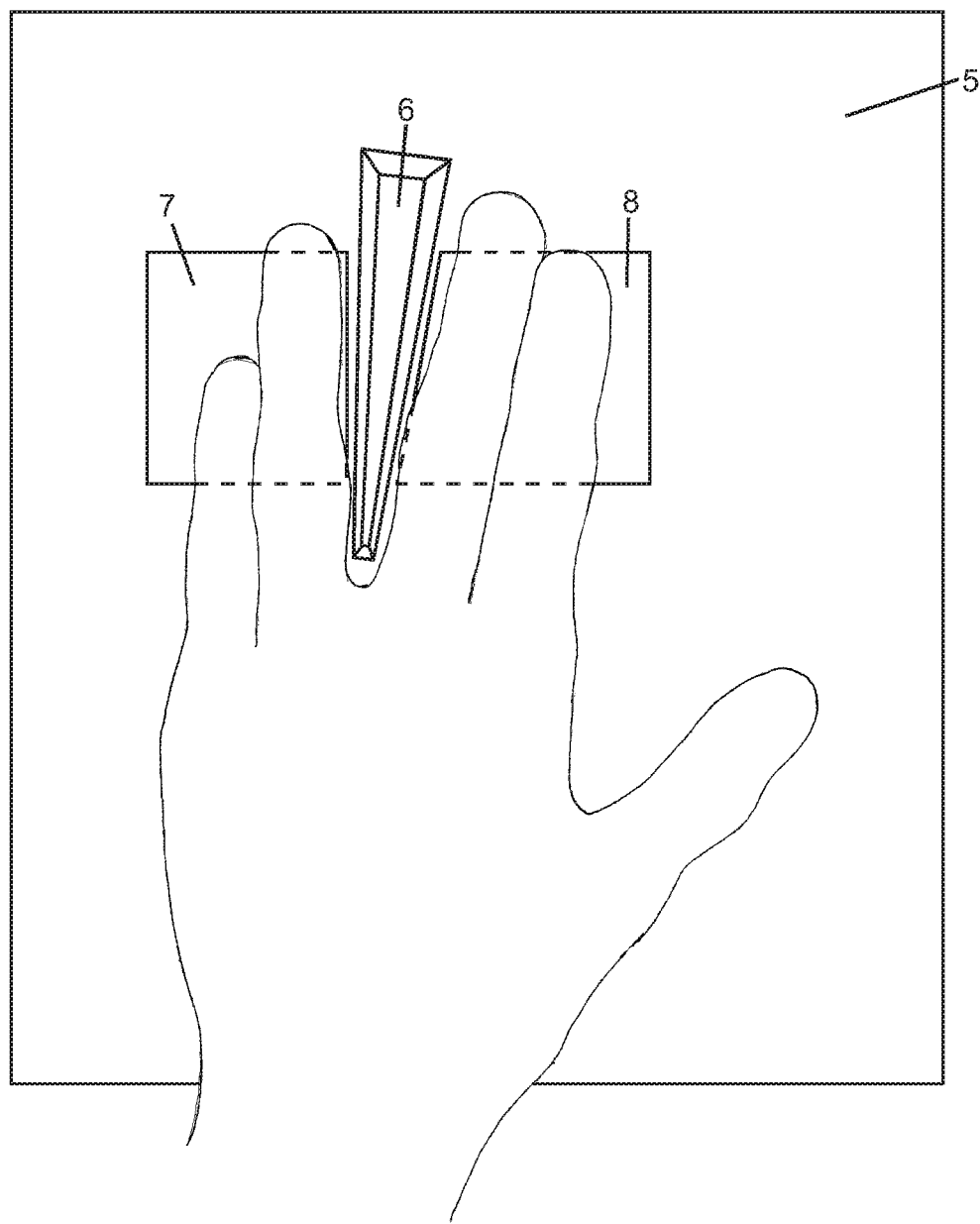
Figure 5:
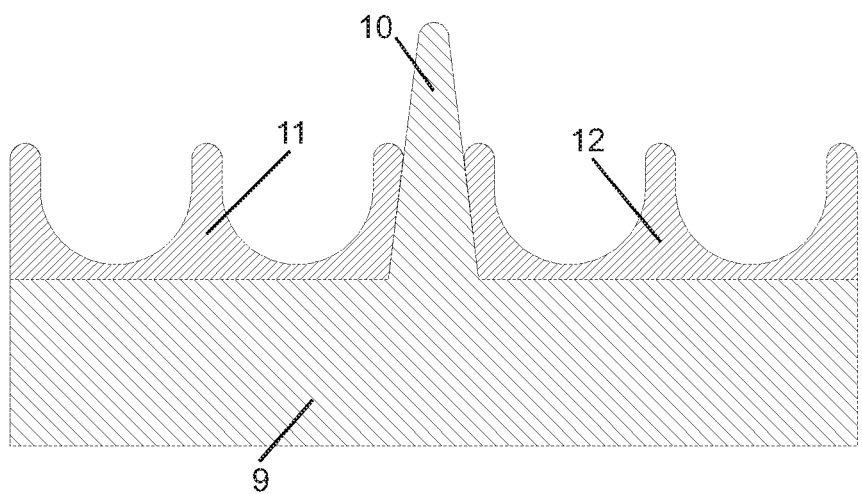

The invention is in the following explained in connection with embodiments shown in the drawings in which:

FIG. 1 is a perspective view of a hand contact body of a first embodiment of a bioelectrical impedance measuring apparatus, FIG. 2 shows the hand contact body of FIG. 1 in a perspective view from another angle, FIG. 3 illustrates the handling of the hand contact body of the bioelectrical impedance measuring apparatus of FIGS. 1 and 2, FIG. 4 shows a hand contact body of an alternative embodiment of the bioelectrical impedance measuring apparatus, and FIG. 5 shows a cross sectional view of the hand contact body of a further alternative embodiment of a bioelectrical impedance measuring apparatus.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

FIGS. 1 to 3 show a hand contact body for a first embodiment of a bioelectrical impedance measurement apparatus. The hand contact body has a partially curved, essentially cylindrical hand seating surface from which projects on one side a bar extending in the longitudinal direction of the cylinder. Furthermore, essentially in the middle of the cylindrical hand contact body 1 a separating wall 2 of electrically insulating material is extending perpendicular to the longitudinal cylinder axis and extends about one half of the cylinder barrel (or in other word extends about 180° around the longitudinal cylinder axis).

On the surface of the hand contact body 1 electrodes are provided in the area which is separated by the separating wall 2, wherein on each side of the separating wall 2 one of the electrodes 3 and 4 is disposed. The electrodes 3 and 4 are connected to alternating current sources, voltage measuring circuits, and amplifiers (not shown) in order to inject according to a specific measuring program an alternating current into specific electrodes and to measure the resulting voltage by other electrodes. The cables which run from the hand contact body 1 to the further components of the bioelectrical impedance measuring apparatus (not shown) are likewise not illustrated because these can be standard components as in prior art apparatus.

FIG. 3 illustrates how to use the hand contact body 1. This hand contact body is grasped by the fingers such that the bar extending in the longitudinal direction of the body abuts the hand in the area of the hand root and such that the hand contact body 1 is embraced by the hand inner surface and the fingers such that the separating wall 2 projects into the space between middle and ring finger. In this manner any electrical contact between the electrodes 3 and 4 is avoided, which electrodes are in contact with the inner surfaces of index and middle finger and ring finger and small finger, respectively. At the same time this arrangement of electrodes 3, 4 and of the separating wall 2 on the hand contact body 1 realizes a symmetrical positioning of the two electrodes 3 and 4 so that injection of the alternating current and the measuring of voltages take place at anatomically equivalent points of the body, namely the same level on parallel finger pairs.

FIG. 4 shows a hand contact body 5 of an alternative bioelectrical impedance measuring apparatus. This hand contact body is formed as a planar hand contact body which may for example be mounted on a column, which column may be connected to the base of the measuring platform or with the standing platform for the feet. Over part of the longitudinal extension of the hand seating surface of the hand contact body 5 an electrically insulating separating wall 6 is extending. On both sides of the separating wall 6 and separated by this separating wall 6, two electrodes 7 and 8 are disposed on the hand seating surface. Also in this arrangement of the hand contact body in each case two fingers come into contact with a respective one of the electrodes 7 and 8, the first pair of fingers being electrically insulated by the separating wall 6 from the other pair of fingers, such that also in this case an anatomically symmetric or equivalent or corresponding positioning of the electrodes 7 and 8 is realized.

FIG. 5 shows a cross-sectional view taken in a direction perpendicular to the longitudinal direction of the separating wall 10 through the hand contact body 9. The separating wall 10 is in this case integrally formed with the hand contact body 9. On both sides of the separating wall 10 an electrode 11 and 12, respectively, is disposed. These electrodes are provided with projections which extend essentially parallel to the direction of the extension of the separating wall 10; these projections are arranged to come into contact with a finger side surface. In the embodiment shown each electrode 11 and 12 is provided with three projections which form finger depressions or finger troughs for two fingers. In this embodiment each finger comes into contact in one of the depressions or troughs of the electrodes 11 and 12 such that besides the inner surface of the fingers also the finger side surfaces come into electrical contact with the electrode. By this a well reproducible electrical contacting is achieved since also the soft skin areas on the finger sides come into contact while the contact on the inner surfaces of the fingers may be deteriorated by thicker skin areas or callus.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and access the reasonably fair scope of the present invention as pertains to any apparatus not materially departing from but outside the literal scope of the invention set forth in the following claims.

What is claimed is:

1. Bioelectrical impedance measuring apparatus for determining composition data of a human body according to predetermined measuring programs, said apparatus comprising:
   a plurality of electrodes which are configured to act as current input electrodes or voltage measurement electrodes depending on the specific measuring program;
   measuring circuitry including alternating current sources, voltage measuring circuits, and a control and analysis unit,
   said control and analysis unit being configured to inject an alternating current from one of the alternating current sources through two of said electrodes into the body, which two electrodes serve as current input electrodes for the specific measuring program, and to determine with two other of said electrodes on different limbs the resulting voltages using the voltage measuring circuits, wherein the two other electrodes serve as voltage measurement electrodes for the specific program, and to determine therefrom the impedance of body segments; and
   two hand contact bodies, each of which is shaped in such a manner and provided with two hand-contacting ones of said electrodes in such a manner that a user, when contacting the hand contact bodies with hands, comes into contact with said two hand-contacting electrodes for each hand on each respective hand contact body,
   each hand contact body including a hand seating surface for placement of a hand inner surface thereon,
   each hand seating surface including an electrically insulating separating wall formed of electrically insulative material and dimensioned to extend at least substantially along the length of at least one finger of a pair of adjacent fingers of a respective one of the hands, said separating wall projecting from the seating surface to extend a height that positions the wall in a space between the fingers when the respective one of the hands is placed on the hand seating surface to thereby prevent direct contact between the fingers and to separate and electrically insulate the fingers from each other,
   one of the two hand-contacting electrodes of each hand contact body being disposed on each side of the separating wall such that, when the respective hand is placed on the hand seating surface, each of the hand-contacting electrodes comes into contact with at least one finger placed on the respective side of the wall.

2. Bioelectrical impedance measuring apparatus according to claim 1,
   each hand seating surface being essentially formed as a plane.

3. Bioelectrical impedance measuring apparatus according to claim 1,
   each hand seating surface being at least partially curved such that it may be grasped by a hand.

4. Bioelectrical impedance measuring apparatus according to claim 1,
   each of said hand-contacting electrodes including a projection which extends essentially parallel to the respective separating wall and which is configured to, when a hand is placed on the respective hand seating surface, abut against a side surface of a finger.

5. Bioelectrical impedance measuring apparatus according to claim 4,
   each of said hand-contacting electrodes including two elongated finger depressions extending essentially parallel to the respective separating wall,
   each of said finger depressions being configured to establish contact to finger side surfaces of a finger placed therein.

6. Bioelectrical impedance measuring apparatus according to claim 1,
   said pair of adjacent fingers including a middle finger and a ring finger.

* * * * *